(12) United States Patent
Beutler et al.

(10) Patent No.: US 8,410,292 B2
(45) Date of Patent: Apr. 2, 2013

(54) EPOXY-GUAIANE DERIVATIVES AND TREATMENT OF CANCER

(75) Inventors: John A. Beutler, Union Bridge, MD (US); Ranjala Ratnayake, Gainesville, FL (US); David Covell, Chevy Chase, MD (US); Tanya R. Johnson, Germantown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 313 days.

(21) Appl. No.: 12/811,245

(22) PCT Filed: Dec. 30, 2008

(86) PCT No.: PCT/US2008/088529
§ 371 (c)(1),
(2), (4) Date: Jul. 29, 2010

(87) PCT Pub. No.: WO2009/088854
PCT Pub. Date: Jul. 16, 2009

(65) Prior Publication Data
US 2010/0286259 A1    Nov. 11, 2010

Related U.S. Application Data

(60) Provisional application No. 61/018,938, filed on Jan. 4, 2008, provisional application No. 61/082,850, filed on Jul. 23, 2008.

(51) Int. Cl.
C07D 311/94     (2006.01)
A61K 31/352     (2006.01)
(52) U.S. Cl. ..... 549/386; 549/27; 540/581; 514/214.03; 514/431; 514/450
(58) Field of Classification Search ............... None
See application file for complete search history.

(56) References Cited

U.S. PATENT DOCUMENTS

| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |

FOREIGN PATENT DOCUMENTS
EP    1 749 830 A1    2/2007

OTHER PUBLICATIONS

Ratnayake et al., *Org. Ltr.*, 11 (1), 57-60 (2009).
Rothman et al., *Am. J. Primatol.*, 68 (7), 675-691 (2006).
Sutthivaiyakit et al., *Tetrahedron*, 59, 9991-9995 (2003).
Szoka et al., *Ann. Rev. Biophys. Bioeng.*, 9, 467-508 (1980).
Wasserman et al., *Cancer*, 36, 1258-1268 (1975).

*Primary Examiner* — Bernard Dentz
(74) *Attorney, Agent, or Firm* — Leydig, Voit & Mayer, Ltd.

(57) ABSTRACT

Disclosed are englerins and derivatives (I) thereof useful in the treatment of a number of cancers, particularly renal cancer, as well as pharmaceutical compositions and method of treating a patient with the use of these derivatives. The englerins, for example Englerin A and Englerin B, can be isolated from the plant *Phyllanthus engleri* or produced by synthetic methods. An example of the englerin derivative is 2'-chloroenglerin A, which has the structure (II), wherein double bond 'a' is E, Z, or a mixture of E and Z.

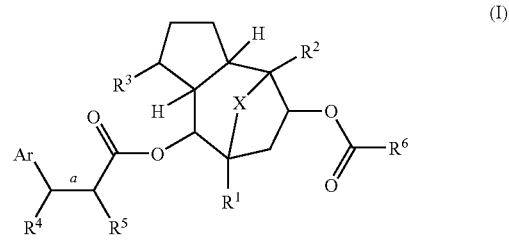

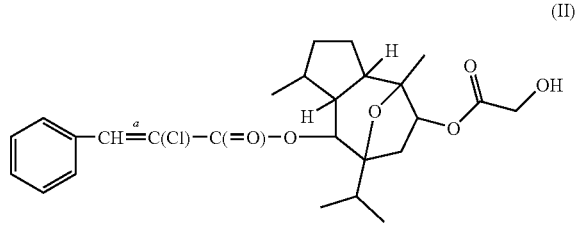

40 Claims, 5 Drawing Sheets

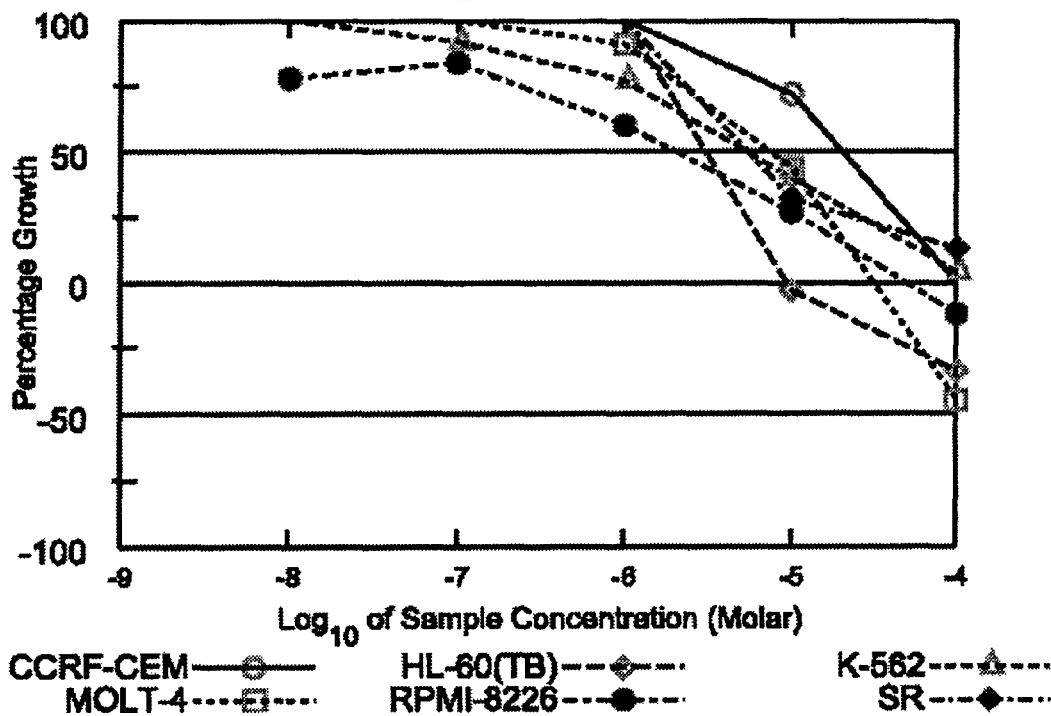
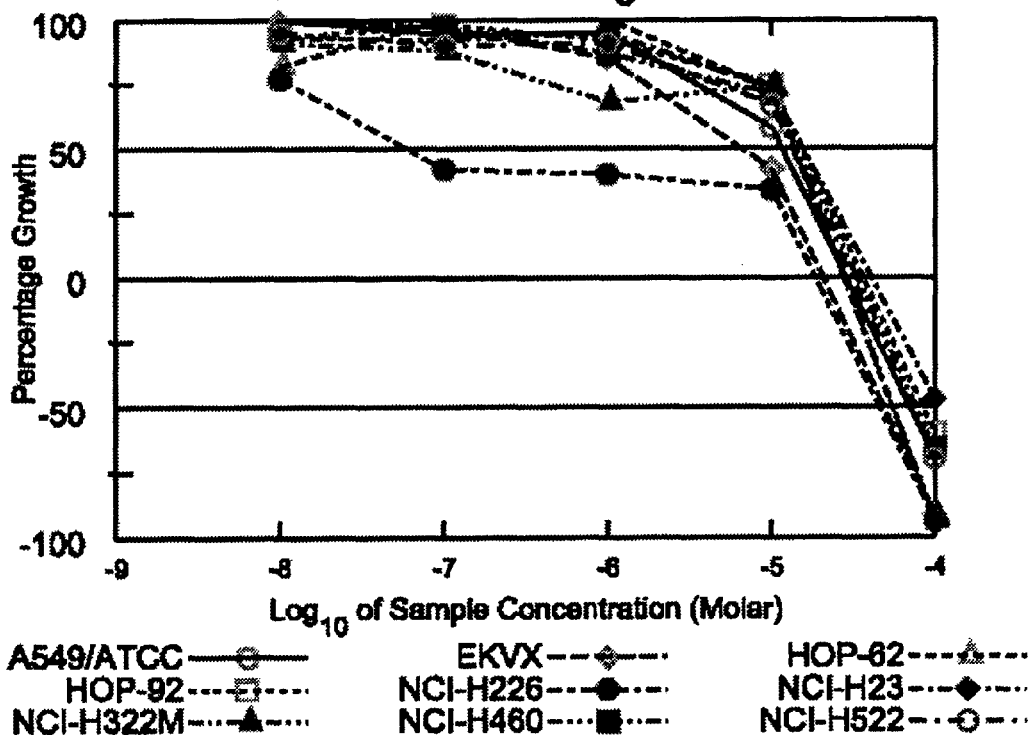

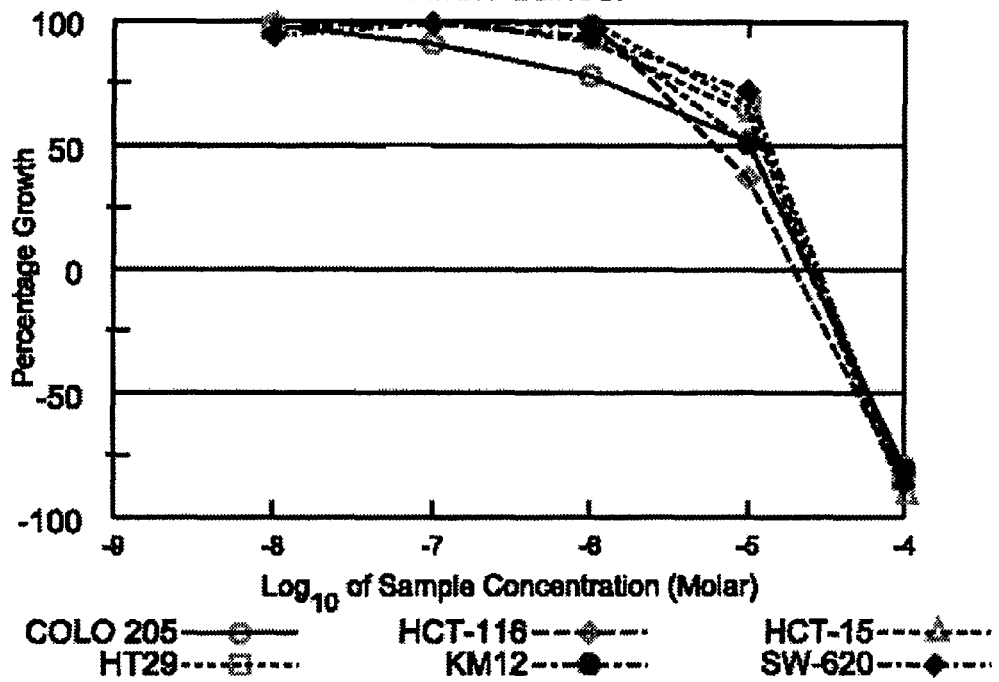
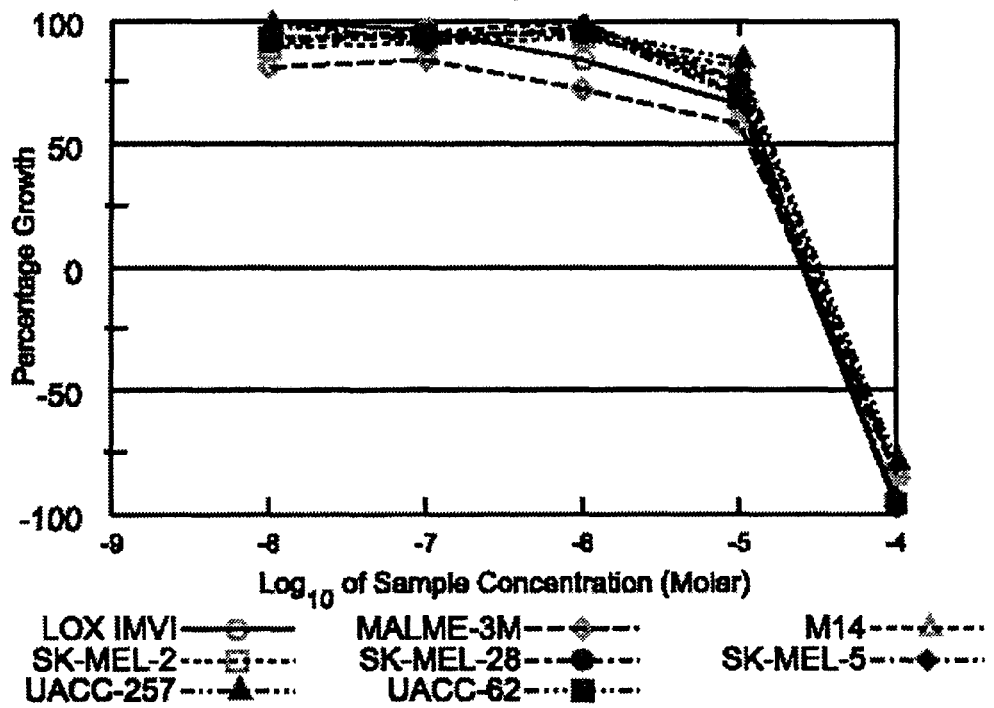

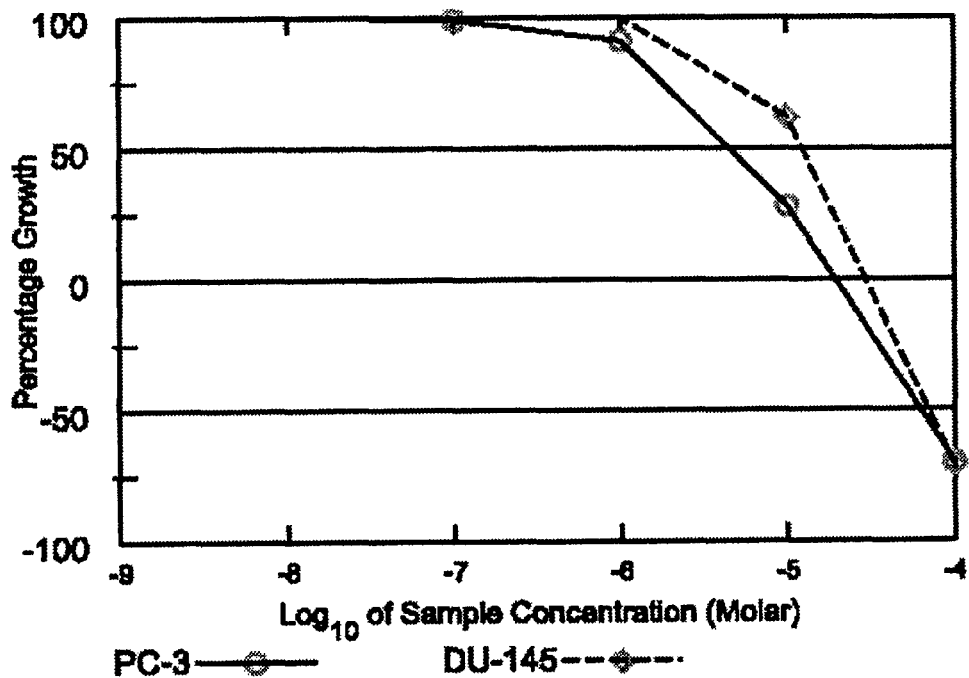
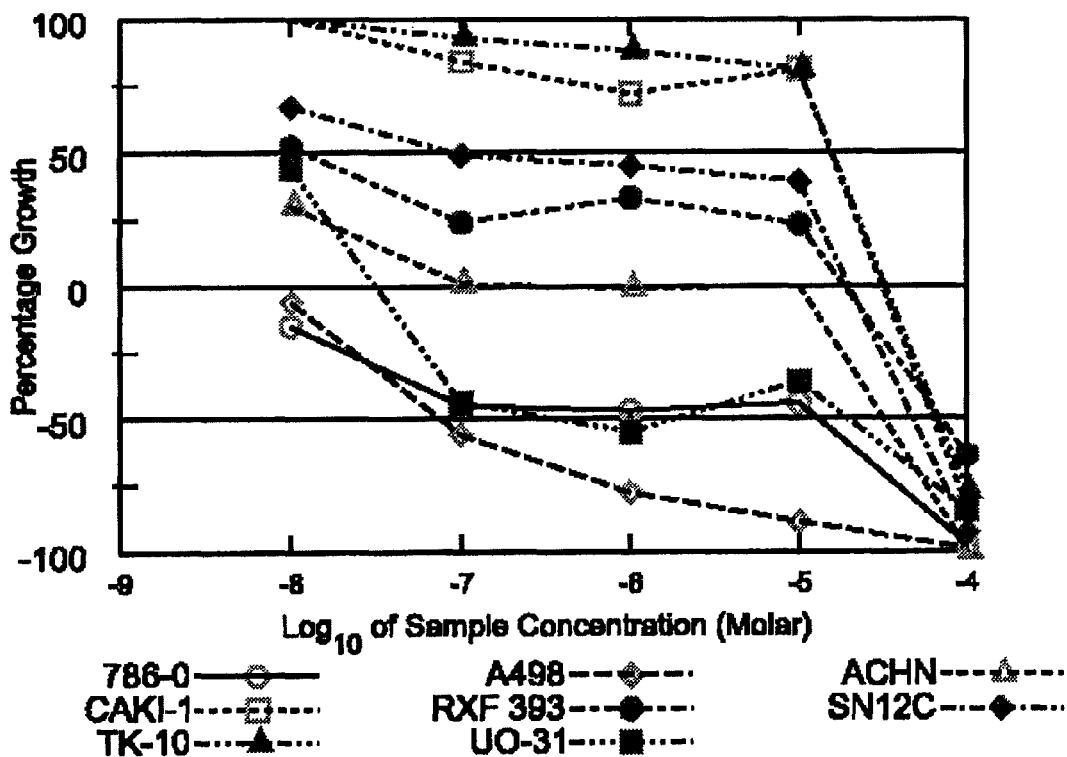

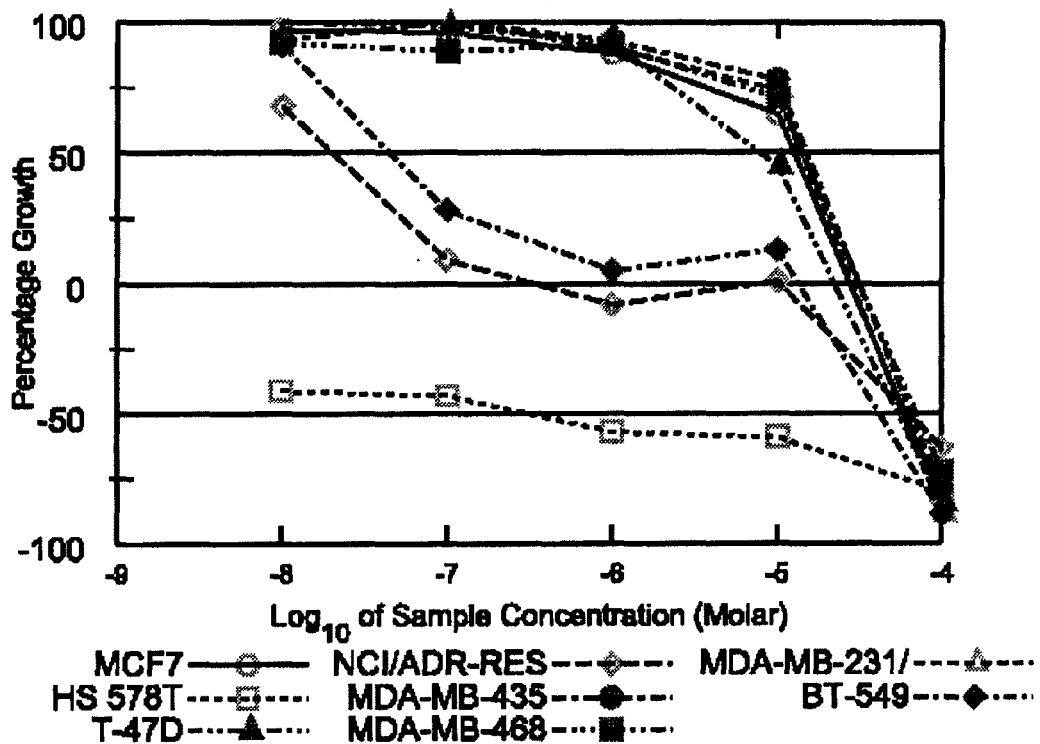
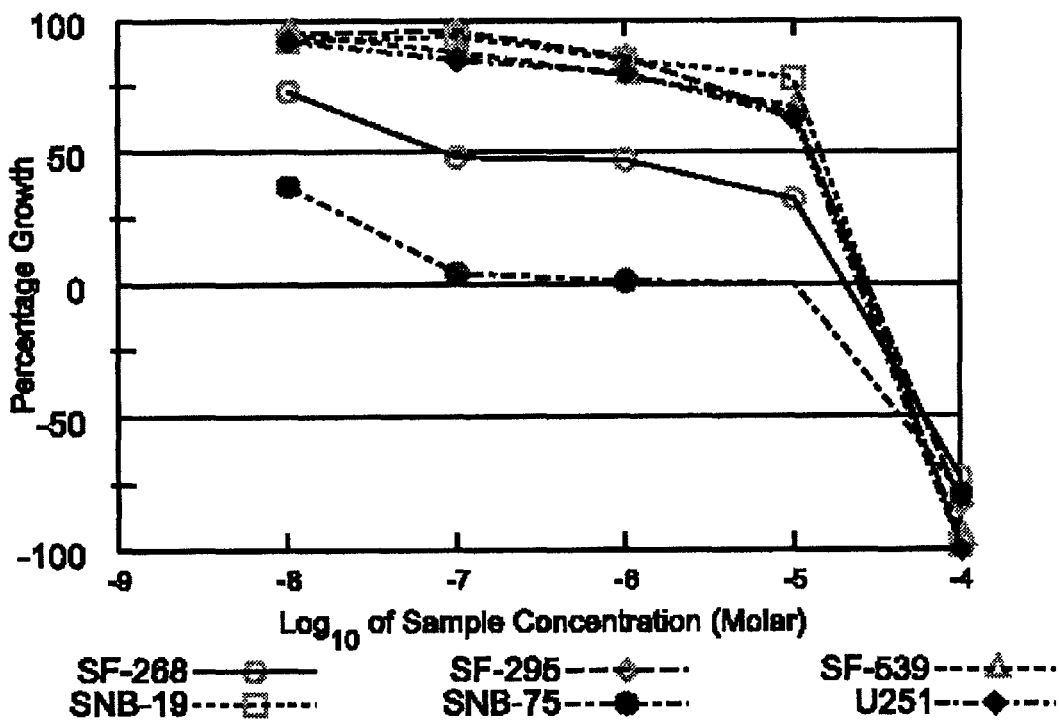

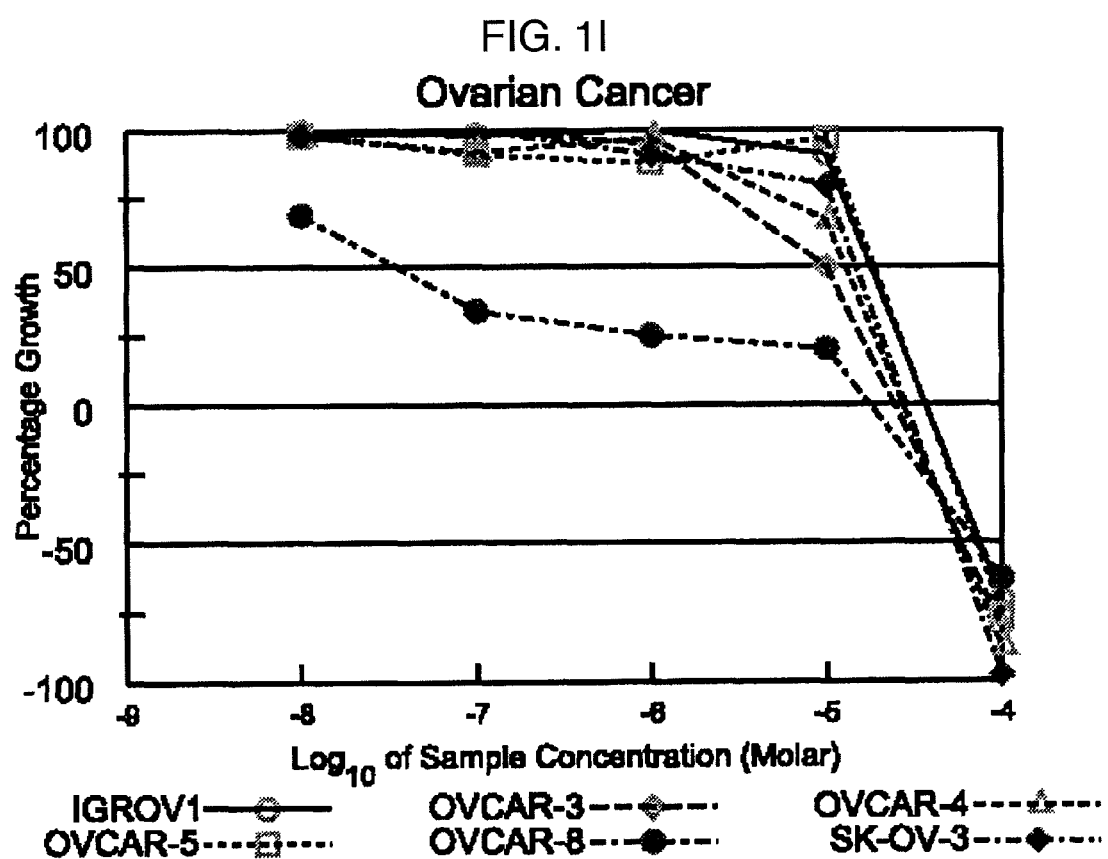

EPOXY-GUAIANE DERIVATIVES AND TREATMENT OF CANCER

CROSS-REFERENCE TO RELATED APPLICATIONS

This application claims the benefit of U.S. Provisional Patent Application Nos. 61/018,938, filed Jan. 4, 2008 and 61/082,850, filed Jul. 23, 2008, the disclosures of which are incorporated by reference.

BACKGROUND OF THE INVENTION

Cancer is a major cause of death; for example, renal cancer is an important contributor to morbidity and mortality with an estimated 51,190 new cases and 12,890 deaths reported in the United States for 2007. Attempts have been made to identify and isolate medicinal products for cancer treatment from plant materials. For example, a large number of *Phyllanthus* species have been found in tropical and subtropical regions of the world and some have been used in traditional medicines.

Accordingly, there is a desire to identify or produce new treatments for cancer, particularly renal cancer.

BRIEF SUMMARY OF THE INVENTION

The invention provides isolated or purified compounds of the formula:

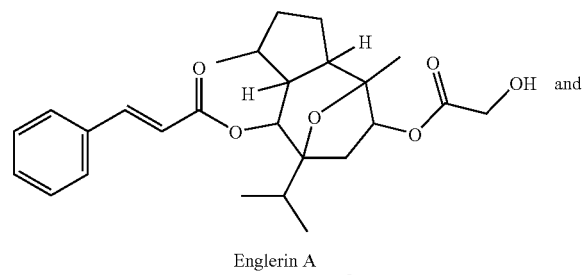

Englerin A

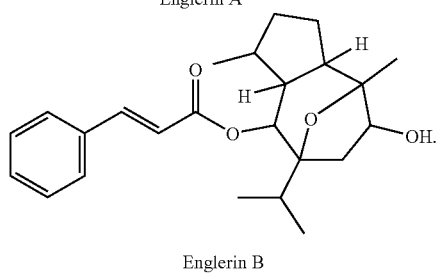

Englerin B

The present invention also provides a compound of the formula (I):

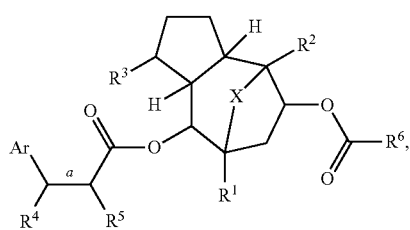

(I)

or an epimer thereof; wherein
Ar is an aryl group, optionally substituted with a $C_1$-$C_6$ alkyl, $C_1$-$C_6$ hydroxyalkyl, $C_1$-$C_6$ alkoxy, halo, or nitro;
X is O, NH, or S;
$R^2$ and $R^3$ are independently a $C_1$-$C_6$ alkyl;
$R^1$ is isopropyl or isopropylidenyl;
"a" is a single bond or a double bond;
when "a" is a double bond, $R^4$ is hydrogen, and $R^5$ is halo or H;
when "a" is a single bond, $R^4$ is selected from the group consisting of halo,
hydroxy, or $C_1$-$C_6$ alkoxy, and $R^5$ is halo or H;
and $R^6$ is $C_1$-$C_6$ alkyl or hydroxy $C_1$-$C_6$ alkyl.

The present invention further provides a pharmaceutical composition comprising a pharmaceutically acceptable carrier and a compound of the invention. The present invention also provides a method of treating cancer, particularly renal cancer in an animal comprising administering to the animal an effective amount of the compound.

BRIEF DESCRIPTION OF THE SEVERAL VIEWS OF THE DRAWINGS

FIG. 1A-1I depict the dose response curves for englerin A against various cancer cell lines in a 60-cell test. FIG. 1A depicts the dose response curves against leukemia cell lines. FIG. 1B depicts the dose response curves against non-small cell lung cancer cell lines. FIG. 1C depicts the dose response curves against colon cancer cell lines. FIG. 1D depicts dose response curves against melanoma cell lines. FIG. 1E depicts dose response curves against prostate cancer cell lines. FIG. 1F depicts dose response curves against renal cancer cell lines. FIG. 1G depicts does response curves against breast cancer cell lines. FIG. 1H depicts dose response curves against CNS cancer cell lines. FIG. 1I depicts dose response curves against ovarian cancer cell lines.

DETAILED DESCRIPTION OF THE INVENTION

In accordance with an embodiment, the invention provides isolated or purified compounds of the formulas:

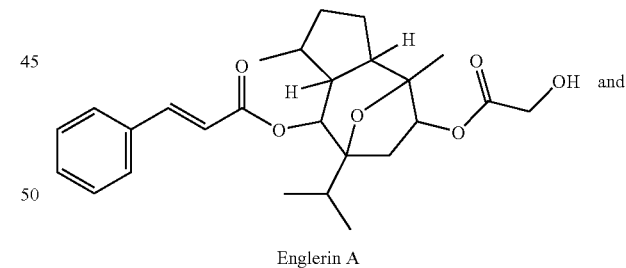

Englerin A

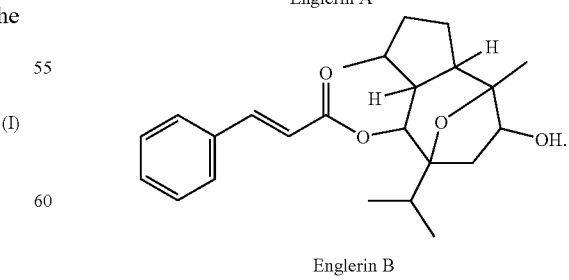

Englerin B

The compounds above can be isolated or purified from natural sources, for example, from the root bark and stem bark of the plant *Phyllanthus engleri* Pax (Euphorbiaceae). This species has a long history as a toxic plant. The book "Common Poisonous Plants of East Africa" (B. Verdcourt & E. C. Trump, 1969) reports that the root and bark of this plant are toxic and lethal when smoked. This property has been used for committing suicide. Experimental work has found that the ethanolic extract is toxic to rabbits by oral and intravenous routes. The bark and root are toxic to sheep and cattle. The poisonous principles were not identified.

The above compounds can be isolated from the plant by any suitable method, for example, by solvent extraction and chromatography, as illustrated in the Examples. In accordance with an embodiment of the invention, the isolated or purified compound has a purity of at least 50% or more, for example, 60% or more, 70% or more, 80% or more, or 90% or more. For example, the isolated or purified compounds or epimers can have a purity of about 60% to 100%, preferably from about 80% to about 99%, and more preferably from about 90% to 100% by weight.

In accordance with another embodiment, the invention provides a compound of the formula (I):

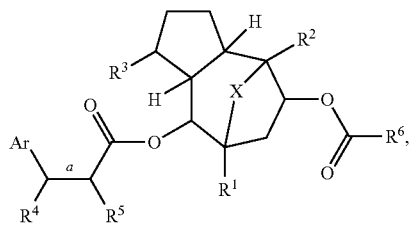

(I)

or an epimer thereof; wherein

Ar is an aryl group, optionally substituted with $C_1$-$C_6$ alkyl, $C_1$-$C_6$ hydroxyalkyl, $C_1$-$C_6$ alkoxy, halo, or nitro;

X is O, NH, or S;

$R^2$ and $R^3$ are independently a $C_1$-$C_6$ alkyl;

$R^1$ is isopropyl or isopropylidenyl;

"a" is a single bond or a double bond;

when "a" is a double bond, $R^4$ is hydrogen, and $R^5$ is halo or H when "a" is a single bond, $R^4$ is selected from the group consisting of halo, hydroxy, or $C_1$-$C_6$ alkoxy and $R^5$ is halo or H;

and $R^6$ is $C_1$-$C_6$ alkyl or hydroxy $C_1$-$C_6$ alkyl.

In a specific embodiment, $R^6$ is hydroxy $C_1$-$C_6$ alkyl, particularly $C_1$-$C_3$ hydroxyalkyl. In accordance with an embodiment, the compound of formula (I) is

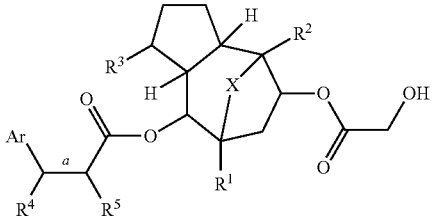

or an epimer thereof.

In accordance with any of the embodiments, $R^5$ can be halo, i.e., fluoro, chloro, bromo, or iodo, particularly chloro.

In any of the embodiments of the invention, Ar can be phenyl, naphthyl, or anthracenyl, phenyl, optionally substituted with $C_1$-$C_6$ alkyl, $C_1$-$C_6$ hydroxyalkyl, $C_1$-$C_6$ alkoxy, halo, or nitro. In a particular embodiment, Ar is phenyl, optionally substituted with $C_1$-$C_6$ alkyl, $C_1$-$C_6$ hydroxyalkyl, $C_1$-$C_6$ alkoxy, halo, or nitro.

In any of the embodiments of the invention, X is preferably O.

In any of the embodiments of the invention, $R^1$ is particularly isopropyl.

In any of the embodiments of the invention, "a" is a double bond or single bond. When "a" is a double bond, the double bond can be E, Z, or a mixture of E and Z (i.e., E/Z). In embodiments where "a" is a single bond, $R^4$ is hydroxy, chloro, or ethoxy.

In another embodiment, the invention provides a compound of formula (I) or epimer thereof, wherein $R^6$ is $C_1$-$C_6$ alkyl, particularly, $C_1$-$C_3$ alkyl.

In any of the embodiments of the invention, $R^2$ and $R^3$ are particularly methyl. Specific examples of the compound of formula I are:

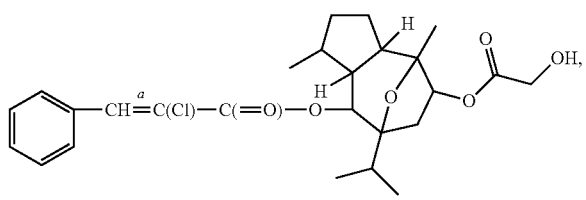

2'-Chloroenglerin A

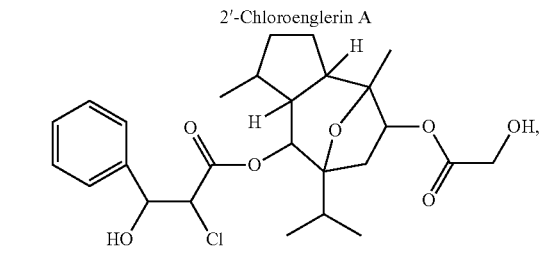

2'-Chloro, 3'-hydroxydihydroenglerin A (epimers 1, 2, 3, or 4)

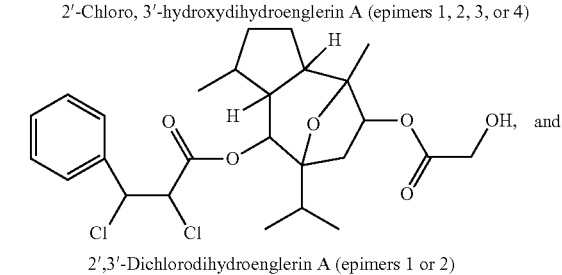

2',3'-Dichlorodihydroenglerin A (epimers 1 or 2)

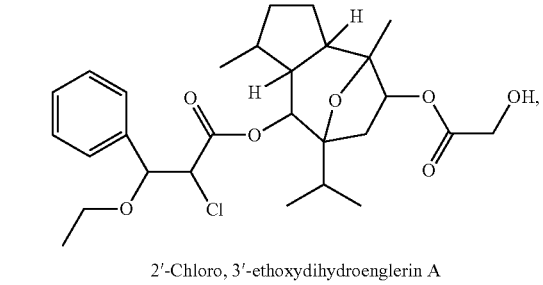

2'-Chloro, 3'-ethoxydihydroenglerin A wherein the double bond "a" in 2'-chloroenglerin A can be E, Z, or a mixture of E and Z. 2'-chloro,3'-hydroxydihydroenglerin A (epimers 1-4) have the same planar structure but are epimers of one another. 2',3'-dichlorodihydroenglerin A (epimers 1 and 2) have the same planar structure but are epimers of each other.

The compounds of formula I can be prepared by any suitable synthetic methodology. For example, in a hemisynthetic route, various ester groups [Ar—C($R^4$)-a-C($R^5$)—C(=O)—O—] can be placed on the guaiane derivative after hydrolysis of the naturally occurring ester groups. Esterification can be carried out on the hydroxyl group by methods known to those skilled in the art, for example, through the use of an acid chloride or acid anhydride and a suitable base. The desired ester moieties can be prepared from suitable cinnamoyl moieties. Halogenated englerins can be prepared by halogenating the isolated or purified englerins or during the isolation or purification.

The invention also provides a pharmaceutical composition comprising a pharmaceutically acceptable carrier and a compound or epimer as described above. The invention also provides a method of treating cancer in an animal comprising administering to the animal an effective amount of a compound or epimer of any of the embodiments described above. The cancer can be any suitable cancer, for example, renal cancer, ovarian cancer, breast cancer, CNS cancer, leukemia, prostate cancer, non-small cell lung cancer, colon cancer, or melanoma, particularly renal cancer, CNS cancer, breast cancer, and ovarian cancer.

In accordance with an embodiment of the invention, englerins, particularly englerin A, 2'-chloroenglerin A, 2'-chloro,3'-hydroxydihydroenglerin A (epimers 1 and 2), and 2',3'-dichlorodihydroenglerin A (epimers 1 and 2), are active against, e.g., decrease the growth of, renal cancer cell lines, e.g., 786-0, A-498, ACHN, CAKI-1, RXF 393, SN 12C, and UO-31. 2'-Chloro,3'-hydroxydihydroenglerin A (epimers 3 and 4) are active against, e.g., decrease the growth of, the renal cancer cell line UO-31. In accordance with an embodiment, englerin A, 2'-chloroenglerin A, 2'-chloro, 3'-hydroxydihydroenglerin A (epimers 1 and 2), and 2',3'-dichlorodihydroenglerin A (epimers 1 and 2) are active against, e.g., decrease the growth of, breast cancer cell lines, e.g., HS 578T, NCI/ADR-RES, and BT-549. In accordance with an embodiment of the invention, englerin A, 2'-chloroenglerin A, 2'-chloro, 3'-hydroxydihydroenglerin A (epimers 1 and 2), and 2',3'-dichlorodihydroenglerin A (epimers 1 and 2) are active against CNS cancer cell lines, e.g., SF-268, SF-295, and/or SNB-75. In accordance with an embodiment, englerin A, 2'-chloroenglerin A, 2'-chloro, 3'-hydroxydihydroenglerin A (epimers 1 and 2), and 2',3'-dichlorodihydroenglerin A (epimers 1 and 2) are active against, e.g., decrease the growth of, ovarian cancer cell lines, e.g., OVCAR-8. For example, these compounds have a $GI_{50}$ or $IC_{50}$ of 1 µM or less, preferably 0.1 µM or less.

As used herein, the term "treat" does not necessarily imply complete elimination of a cancer. Rather, there are varying degrees of treatment of which one of ordinary skill in the art recognizes as having a benefit or therapeutic effect. In this respect, the cancer can be treated to any extent through the present inventive method. For example, at least 10% (e.g., at least 20%, 30%, or 40%) of the growth of a cancerous tumor desirably is inhibited upon administration of a compound described herein. Preferably, at least 50% (e.g., at least 60%, 70%, or 80%) of the growth of a cancerous tumor is inhibited upon administration of a compound described herein. More preferably, at least 90% (e.g., at least 95%, 99%, or 100%) of the growth of a cancerous tumor is inhibited upon administration of a compound described herein. In addition or alternatively, the inventive method may be used to inhibit metastasis of a cancer.

In accordance with the invention, the term "animal" includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The compound (or epimer thereof) is administered in a dose sufficient to treat the cancer. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response, e.g., as determined by measuring cancer-specific antigens or other measurable parameters related to the tumor load of a patient.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-

630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

An compound or epimer of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound or epimer of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound or epimer in the pharmaceutical formulations can vary, e.g., from less than about 1%, usually at or at least about 10%, to as much as 20% to 50% or more by weight, and can be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The following examples further illustrate the invention but, of course, should not be construed as in any way limiting its scope.

Example 1

This example demonstrates a method of isolation of englerin A and englerin B from *Phyllanthus engleri* root bark.

Dried root bark is ground and extracted overnight with 1:1 (v/v) of methylene chloride:methanol, then rinsed with methanol. The combined solvents are evaporated to dryness in vacuo. 14.85 grams of extract is obtained from 201 grams of dried root bark.

Initial fractionation: 7.1 grams of the extract is dissolved in methylene chloride-methanol and coated by evaporation on 70 grams of diol bonded phase media. This material is mixed with hexane and further evaporated to yield a flowable powder free of residual solvent. The coated media is packed over a similar volume of uncoated media in a vacuum filtration apparatus and eluted successively with hexane, methylene chloride, ethyl acetate, acetone, and methanol (750 mL of each solvent). The successive fractions are evaporated in vacuo giving a total mass recovery of 6.4 grams (92%). Fractions are tested for cell growth inhibition using A498/UO-31 (renal) and SF-295 (CNS) cell lines. The methylene chloride fraction (1.8 grams) possesses the desired activity.

Flash chromatography: 1.7 g of the compound methylene chloride fraction is dissolved in 25 mL of chloroform and separated on a 5×16 cm silica gel flash chromatography column, eluting with chloroform (1.5 L), then a mixture of chloroform-methanol 4:1 (500 mL) and lastly, 1:1 chloroform-methanol (500 mL) collecting in 25-50 mL fractions. Fractions are examined by silica gel thin layer chromatography and combined (fractions A-F) based on similar TLC patterns (vanillin-sulfuric acid spray reagent). Fraction B (1.39 g), collected in tubes 5-11 and fraction C (115.0 mg) collected in tubes 12-15 demonstrate the highest level of cell growth inhibition. The major triterpenes in fraction B (1.39 g) are easily removed by dissolving fraction B in methanol and passing through a diol (SPE) cartridge and eluting with methanol (fraction B'). Fraction B' and fraction C contain englerins A and B as the major compounds.

High performance liquid chromatography: 63 mg of the above fraction C is dissolved in 0.9 mL of methanol and injected in 100 μL aliquots (~7 mg/injection) onto a 250×10 mm Varian Dynamax Microsorb 60-8 $C_{18}$ HPLC column. The detector wavelength is 225 nm. Solvent elution conditions (4.2 mL/min) begin with 75% methanol, running isocratic for 5 minutes and switching to a linear gradient from 5 minutes from 75% to 85% at 10 minutes and then to 100% at 20 minutes. The column is flushed with 100% methanol for a further 10 minutes. The two major UV-absorbing peaks are collected and evaporated in vacuo. Englerin A (35.4 mg) elutes at approximately 17.7 minutes while englerin B (1.9 mg) elutes at 17.0 minutes under these conditions.

Further HPLC: The same conditions are used to purify fraction B' to provide englerin A.

Example 2

This Example demonstrates another method of isolation of englerins A and B from *Phyllanthus engleri* stem bark. Dried stem bark is ground and extracted overnight with 1:1 (v/v) of methylene chloride:methanol, then rinsed with methanol. The combined solvents are evaporated to dryness in vacuo. 16.57 grams of extract is obtained from 387 grams of dried bark.

Initial fractionation: 3.01 grams of the extract is dissolved in methylene chloride-methanol and coated by evaporation on 33 grams of diol bonded phase media. This material is mixed with hexane and further evaporated to yield a flowable powder free of residual solvent. The coated media is packed over a similar volume of uncoated media in a vacuum filtration apparatus and eluted successively with hexane, methylene chloride, ethyl acetate, acetone, and methanol. The successive fractions are evaporated in vacuo and tested for cell growth inhibition using UO-31 (renal) and SF-295 (CNS) cell lines. The methylene chloride fraction (853 mg) possesses the desired activity.

Flash chromatography: 0.732 g of the methylene chloride fraction is dissolved in 10 mL of chloroform and separated on a 5×14 cm silica gel flash chromatography column, eluting with chloroform (1 L), then a mixture of chloroform-methanol 4:1 (500 mL) and lastly, 1:1 chloroform-methanol (500 mL) collecting in 25-50 mL fractions. Fractions are examined by silica gel thin layer chromatography and combined based on similar TLC patterns (vanillin-sulfuric acid spray reagent) Fraction E (232.4 mg), which comprises tubes 25-31, demonstrates the highest level of cell growth inhibition.

High performance liquid chromatography: 232 mg of the above fraction E is dissolved in 1.5 mL of dimethyl sulfoxide/methanol and injected in 250 μL aliquots (~40 mg/injection) onto a 250×21.4 mm Varian Dynamax Microsorb 60-8 $C_{18}$ HPLC column. The detector wavelength is 225 nm. Solvent elution conditions (at 20 mL/min) begin with 75% methanol, with a linear gradient from 5 minutes from 75% to 85% at 32 minutes, thence to 100% at 36 minutes, and returns to initial conditions at 45 minutes. The two major peaks are collected and evaporated in vacuo. Englerin A elutes at approximately 22 minutes and englerin B at 25 minutes under these conditions. Table 1 sets forth the $^{13}C$ NMR data for the various englerins.

Example 3

This example demonstrates a method of obtaining halogenated englerins from *Phyllanthus engleri* bark. Halogenation takes place during extraction or purification of englerins.

Dried root bark is ground and extracted overnight with 1:1 (v/v) of methylene chloride:methanol, then rinsed with methanol. The combined solvents are evaporated to dryness in vacuo. 14.85 grams of extract is obtained from 201 grams of dried root bark.

Initial fractionation: 2.61 grams of the extract is dissolved in methylene chloride-methanol and coated by evaporation on 27 grams of diol bonded phase media. This material is mixed with hexane and further evaporated to yield a flowable powder free of residual solvent. The coated media is packed over a similar volume of uncoated media in a vacuum filtration apparatus and eluted successively with hexane, methylene chloride, ethyl acetate, acetone, and methanol. The successive fractions are evaporated in vacuo and tested for cell growth inhibition using UO-31 and SF-295 cell lines. The methylene chloride fraction (612 mg) possesses the desired activity.

Flash chromatography: 515.5 mg of the compound methylene chloride fraction is dissolved in 10 mL of chloroform, which is suspected to contain a chlorinating impurity including HCl, and separated on a 5×14 cm silica gel flash chromatography column, eluting with chloroform, then a mixture of chloroform-methanol 5:1 and lastly, methanol. Fractions are examined by silica gel thin layer chromatography and combined based on similar TLC patterns. Fraction E (194 mg), which comprise tubes 15-17, demonstrate the highest level of cell growth inhibition.

High performance liquid chromatography: 50 mg of the above fraction E is dissolved in 0.5 mL of dimethyl sulfoxide and injected in 10-50 microliter aliquots onto a 10×250 mm Varian Dynamax Microsorb 60-8 $C_{18}$ HPLC column. The detector wavelength is 225 nm. Solvent elution conditions begin with 75% methanol, with a linear gradient from 5 minutes from 75% to 85% at 32 minutes, thence to 100% at 36 minutes, and returns to initial conditions at 40 minutes. Peaks are collected and evaporated in vacuo. 2'-Chloroenglerin A elutes at approximately 28 minutes under these conditions, while 2'-Chloro,3'-hydroxydihydroengerin A (epimers 1 and 2) elute at 9 and 11 minutes, respectively. 2',3'-Dichlorodihydroenglerin A (epimer 1) elutes at 23 minutes, but is not completely resolved from other constituents. From the above 50 mg of material, 2.7 mg of 2'-chloroenglerin A, 1.2 mg of 2'-chloro, 3'-hydroxydihydroenglerin (epimer 1), 0.6 mg of 2'-chloro, 3'-hydroxydihydroenglerin (epimer 2), and 2.2 mg of 2',3'-dichlorodihydroenglerin A (epimer 1) are obtained.

Further HPLC: The sample of 2'-chloroenglerin A obtained above is further purified by HPLC using a Varian Dynamax C8 column, eluting with an isocratic system 80% acetonitrile. 7.5 mg of the impure 2'-chloroenglerin A is purified to yield 4.2 mg of pure 2'-chloroenglerin A.

Example 4

This Example demonstrates a method of isolation of halogenated englerins from *Phyllanthus engleri* bark. Halogenation takes place during the extraction or purification of englerins.

Dried stem bark is ground and extracted overnight with 1:1 (v/v) of methylene chloride:methanol, then rinsed with methanol. The combined solvents are evaporated to dryness in vacuo. 16.57 grams of extract is obtained from 387 grams of dried bark.

Initial fractionation: 3.01 grams of the extract is dissolved in methylene chloride-methanol and coated by evaporation on 33 grams of diol bonded phase media. This material is mixed with hexane and further evaporated to yield a flowable powder free of residual solvent. The coated media is packed over a similar volume of uncoated media in a vacuum filtration apparatus and eluted successively with hexane, methylene chloride, ethyl acetate, acetone, and methanol. The successive fractions are evaporated in vacuo and tested for cell growth inhibition using UO-31 and SF-295 cell lines. The methylene chloride fraction (853 mg) possesses the desired activity.

Flash chromatography: 147.8 mg of the compound methylene chloride fraction is dissolved in 2 mL of chloroform and separated on a 2×16 cm silica gel flash chromatography column, eluting with chloroform, which is also suspected to contain a chlorinating impurity including HCl, then a mixture of chloroform-methanol 4:1 and lastly, methanol. Fractions are examined by silica gel thin layer chromatography and combined based on similar TLC patterns (vanillin-sulfuric acid spray reagent) Fraction F (113.9 mg), which comprises tubes 12-22, demonstrates the highest level of cell growth inhibition. This compound fraction is purified by HPLC as in example 1 to yield further englerin derivatives. Table 1 sets forth the $^{13}$C NMR data for the various englerin derivatives.

The carbon atoms of the various englerins are numbered as follows.

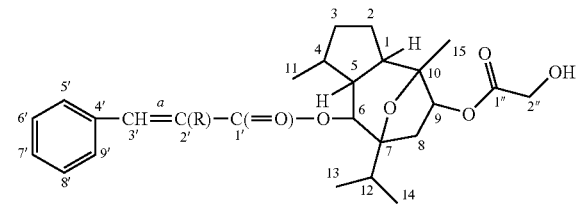

2'-Chloroenglerin A, Englerin A, or Englerin B (to applicable part of the molecule),

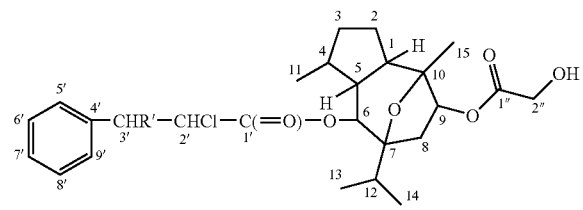

2'-Chloro, 3'-hydroxydihydroenglerin A (epimer 1, 2, 3, or 4).

TABLE 1

| | $^{13}$C NMR $\delta_C$ data for englerins (500 MHz, $d_4$-methanol) | | | | | | | | | |
|---|---|---|---|---|---|---|---|---|---|---|
| # | Compd 1 | Compd 2 | Compd 3 | Compd 4 | Compd 5 | Compd 6* | Compd 7 | Compd 8 | Englerin B | Englerin A |
| 1 | 48.90 | 48.56 | 48.95 | 48.86 | 48.88 | 48.50 | 48.79 | 48.82 | 48.86 | 48.89 |
| 2 | 25.46 | 25.46 | 25.41 | 25.29 | 25.20 | 25.19 | 25.24 | 25.27 | 25.70 | 25.52 |
| 3 | 32.02 | 31.89 | 31.96 | 31.74 | 31.86 | 31.24 | 31.71 | 31.89 | 32.09 | 31.99 |
| 4 | 32.44 | 32.33 | 32.35 | 31.80 | 31.93 | 32.15 | 31.79 | 31.27 | 32.35 | 32.43 |
| 5 | 47.86 | 47.81 | 47.86 | 47.43 | 47.49 | 47.44 | 47.46 | 47.62 | 47.76 | 47.99 |
| 6 | 74.75 | 73.94 | 73.90 | 74.33 | 74.25 | 73.47 | 73.85 | 73.75 | 72.85 | 72.43 |
| 7 | 86.54 | 86.45 | 86.49 | 86.21 | 85.95 | 86.06 | 86.25 | 86.17 | 86.21 | 86.44 |
| 8 | 40.78 | 40.30 | 40.21 | 40.05 | 39.86 | 39.87 | 40.17 | 39.88 | 43.43 | 40.69 |
| 9 | 76.60 | 76.54 | 76.59 | 76.44 | 76.43 | 76.19 | 76.45 | 76.49 | 73.18 | 76.61 |

TABLE 1-continued $^{13}$C NMR $\delta_C$ data for englerins (500 MHz, d$_4$-methanol)

| # | Compd 1 | Compd 2 | Compd 3 | Compd 4 | Compd 5 | Compd 6* | Compd 7 | Compd 8 | Englerin B | Englerin A |
|---|---|---|---|---|---|---|---|---|---|---|
| 10 | 86.16 | 86.06 | 86.04 | 85.93 | 85.11 | 85.68 | 85.95 | 85.92 | 86.76 | 86.01 |
| 11 | 17.17 | 17.16 | 17.18 | 17.01 | 16.84 | 16.86 | 17.10 | 18.15 | 17.33 | 17.27 |
| 12 | 34.05 | 32.73 | 32.20 | 31.91 | 31.19 | 32.00 | 32.39 | 32.19 | 34.58 | 34.04 |
| 13 | 18.56 | 18.38 | 18.33 | 18.15 | 18.06 | 17.17 | 18.28 | 17.29 | 17.92 | 17.77 |
| 14 | 17.69 | 17.54 | 17.49 | 17.48 | 17.25 | 18.08 | 17.52 | 16.96 | 18.78 | 18.59 |
| 15 | 19.20 | 19.17 | 19.17 | 19.05 | 18.55 | 18.83 | 19.09 | 19.09 | 19.50 | 19.25 |
| 1' | 163.45 | 169.13 | 169.06 | 167.23 | 167.05 | 168.70 | 168.27 | 168.17 | 168.37 | 167.26 |
| 2' | 122.85 | 61.40 | 60.87 | 62.85 | 62.79 | 60.61 | 63.54 | 63.48 | 118.94 | 118.80 |
| 3' | 138.88 | 76.48 | 76.29 | 64.72 | 64.63 | 83.31 | 76.14 | 75.97 | 146.60 | 146.75 |
| 3'-OCH$_2$CH$_3$ | | | | | | 65.75 | | | | |
| 3'-OCH$_2$CH$_3$ | | | | | | 15.05 | | | | |
| 4' | 134.18 | 141.69 | 141.58 | 138.65 | 138.60 | 138.05 | 141.06 | 140.99 | 135.65 | 135.62 |
| 5' | 131.84 | 128.40 | 128.32 | 129.26 | 129.31 | 128.90 | 128.67 | 128.69 | 129.29 | 129.33 |
| 6' | 129.71 | 129.30 | 128.53 | 130.01 | 130.02 | 129.09 | 129.63 | 129.63 | 130.04 | 130.06 |
| 7' | 131.60 | 129.40 | 129.35 | 130.59 | 130.67 | ** | 129.69 | 129.76 | 131.59 | 131.64 |
| 8' | 129.71 | 129.30 | 128.53 | 130.01 | 130.02 | 129.09 | 129.63 | 129.63 | 130.04 | 130.06 |
| 9' | 131.84 | 128.40 | 128.32 | 129.26 | 129.31 | 128.90 | 128.67 | 128.69 | 129.29 | 129.33 |
| 1" | 173.97 | 173.96 | 173.98 | 173.93 | 173.95 | 173.46 | 173.95 | 173.95 | | 173.94 |
| 2" | 61.06 | 61.04 | 61.04 | 61.02 | 61.02 | 59.24 | 61.02 | 61.01 | | 61.03 |

*assignments are made with aid of gHMBC correlations;
**overlapping signals prevent unambiguous assignment.
Compd 1. 2'-Chloroenglerin A
Compd 2. 2'-Chloro,3'-hydroxydihydroenglerin A (epimer 1)
Compd 3. 2'-Chloro,3'-hydroxydihydroenglerin A (epimer 2)
Compd 4. 2',3'-Dichlorodihydroenglerin A (epimer 1)
Compd 5. 2',3'-Dichlorodihydroenglerin A (epimer 2)
Compd 6. 2'-Chloro,3'-ethoxydihydroenglerin A
Compd 7. 2'-Chloro,3'-hydroxydihydroenglerin A (epimer 3)
Compd 8. 2'-Chloro,3'-hydroxydihydroenglerin A (epimer 4)

Table 2 sets forth the $^1$H NMR data for englerins.

TABLE 2

$^1$H NMR data for englerins (500 MHz, d$_4$-methanol)

| Englerins # | Compd 1 | Compd 2 | Compd 3 $\delta_H$ (m, J (in Hz)) | Compd 4 | Compd 5 |
|---|---|---|---|---|---|
| 1 | 1.76 (m) | 1.72 (m) | 1.74 (m) | 1.58 (m) | 1.61 (m) |
| 2a | 1.75 (m) | 1.72 (m) | 1.74 (m) | 1.63 (m) | 1.66 (m) |
| 2b | 1.34 (m) | 1.28 (m) | 1.33 (m) | 1.20 (m) | 1.25 (m) |
| 3a | 2.02 (m) | 1.98 (m) | 2.00 (m) | 1.77 (m) | 1.85 (m) |
| 3b | 1.28 (m) | 1.26 (m) | 1.29 (m) | 1.09 (m) | 1.16 (m) |
| 4 | 2.14 (m) | 2.19 (m) | 2.23 (m) | 1.34 (m) | 1.63 (m) |
| 5 | 1.75 (m) | 1.55 (m) | 1.64 (m) | 1.34 (m) | 1.39 (m) |
| 6 | 5.14 (d, 9.5) | 5.02 (d, 10.0) | 5.07 (d, 10.0) | 4.80 (d, 9.5) | 4.79 (d, 10.0) |
| 7 | | | | | |
| 8a | 2.73 (dd, 14.5, 8.0) | 2.45 (dd, 15.0, 8.0) | 2.57 (dd, 15.0, 8.0) | 2.44 (dd, 14.5, 8.0) | 2.43 (dd, 14.5, 8.0) |
| 8b | 1.89 (dd, 14.5, 3.0) | 1.81 (dd, 15.0, 3.0) | 1.90 (dd, 15.0, 3.0) | 1.80 (dd, 14.5, 3.0) | 1.82 (dd, 14.5, 3.0) |
| 9 | 5.27 (dd, 8.0, 3.0) | 5.18 (dd, 8.0, 3.0) | 5.23 (dd, 8.0, 3.0) | 5.12 (dd, 8.0, 3.0) | 5.15 (dd, 8.0, 3.0) |
| 10 | | | | | |
| 11 | 0.93 (d, 7.0) | 0.89 (d, 7.0) | 0.93 (d, 7.0) | 0.56 (d, 6.5) | 0.72 (d, 7.0) |
| 12 | 1.87 (m) | 1.87 (m) | 1.88 (m) | 1.46 (m) | 1.27 (m) |
| 13 | 0.97 (d, 7.0) | 0.95 (d, 7.5) | 0.99 (d, 6.5) | 0.84 (d, 7.0) | 0.64 (d, 7.0) |
| 14 | 1.02 (d, 6.5) | 0.98 (d, 7.0) | 1.01 (d, 6.5) | 0.89 (d, 7.0) | 0.80 (d, 6.5) |
| 15 | 1.199 (s) | 1.16 (s) | 1.19 (s) | 1.10 (s) | 1.11 (s) |
| 1' | | | | | |
| 2' | | 4.40 (d, 9.0) | 4.36 (d, 9.0) | 5.02 (d, 9.5) | 4.98 (d, 10.0) |
| 3' | 7.94 (s) | 4.88 (d, 9.0) | 4.90 (d, 9.0) | 5.31 (d, 9.5) | 5.27 (d, 10.0) |
| 3'-OCH$_2$CH$_3$ | | | | | |
| 3'-OCH$_2$CH$_3$ | | | | | |
| 4' | | | | | |
| 5' | 7.87 (brd, 7.5) | 7.43 (d, 7.0) | 7.44 (dd, 8.0, 2.0) | 7.47 (brdd, 8.0, 3.0) | 7.48 (brdd, 7.5, 2.0) |
| 6' | 7.45 (m) | 7.36 (dd, 8.0, 7.0) | 7.36 (dd, 8.0, 7.0) | 7.37 (m) | 7.37 |

TABLE 2-continued $^1$H NMR data for englerins (500 MHz, d$_4$-methanol)

| | | | | | |
|---|---|---|---|---|---|
| 7' | 7.45 (m) | 7.31 (brd, 8.0) | 7.33 (d, 7.0) | 7.37 (m) | 7.37 |
| 8' | 7.45 (m) | 7.36 (dd, 8.0, 7.0) | 7.36 (dd, 8.0, 7.0) | 7.37 (m) | 7.37 |
| 9' | 7.87 (brd, 7.5) | 7.43 (d, 7.0) | 7.44 (dd, 8.0, 2.0) | 7.47 (brdd, 8.0, 3.0) | 7.48 (brdd, 7.5, 2.0) |
| 1" | | | | | |
| 2" | 4.15 (s) | 4.13 (s) | 4.13 (s) | 4.12 (s) | 4.12 (s) |

| Englerins # | Compd 6 | Compd 7 | Compd 8 $\delta_H$ (m, J (in Hz)) | Englerin B | Englerin A |
|---|---|---|---|---|---|
| 1 | 1.74 (m) | 1.61 (m) | 1.62 (m) | 1.70 (m) | 1.73 (m) |
| 2a | 1.74 (m) | 1.18 (m) | 1.67 (m) | 1.70 (m) | 1.71 (m) |
| 2b | 1.32 (m) | 1.60 (m) | 1.21 (m) | 1.18 (m) | 1.30 (m) |
| 3a | 1.99 (m) | 1.76 (m) | 1.86 (m) | 1.94 (m) | 1.98 (m) |
| 3b | 1.28 (m) | 1.05 (m) | 1.18 (m) | 1.24 (m) | 1.25 (m) |
| 4 | 2.17 (m) | 1.32 (m) | 1.27 (m) | 2.07 (m) | 2.12 (m) |
| 5 | 1.65 (m) | 1.25 (m) | 1.47 (m) | 1.57 (m) | 1.63 (m) |
| 6 | 5.08 (d, 10.0) | 4.81 (d, 7.0) | 4.81 (d, 9.5) | 5.06 (d, 10.0) | 5.10 (d, 10.0) |
| 7 | | | | | |
| 8a | 2.58 (dd, 15.0, 8.5) | 2.42 (dd, 15.0, 8.0) | 2.40 (dd, 14.5, 8.0) | 2.62 (dd, 14.0, 8.0) | 2.67 (dd, 14.0, 8.0) |
| 8b | 1.88 (dd, 15.0, 3.0) | 1.81 (dd, 15.0, 3.0) | 1.75 (dd, 14.5, 3.0) | 1.73 (dd, 14.0, 2.5) | 1.86 (dd, 14.0, 2.5) |
| 9 | 5.24 (dd, 8.5, 3.0) | 5.11 (dd, 8.0, 3.0) | 5.15 (dd, 8.0, 3.0) | 4.02 (dd, 8.0, 2.5) | 5.23 (dd, 8.0, 2.5) |
| 10 | | | | | |
| 11 | 0.92 (d, 7.0) | 0.62 (d, 7.0) | 0.64 (d, 7.0) | 0.90 (d, 7.0) | 0.92 (d, 7.0) |
| 12 | 1.93 (m) | 1.66 (m) | 1.82 (m) | 1.86 (m) | 1.86 (m) |
| 13 | 1.01 (d, 7.0) | 0.89 (d, 7.0) | 0.77 (d, 6.5) | 1.02 (d, 7.0) | 1.00 (d, 7.0) |
| 14 | 1.01 (d, 7.0) | 0.92 (d, 6.5) | 0.78 (d, 7.0) | 0.95 (d, 7.0) | 0.95 (d, 7.0) |
| 15 | 1.18 (s) | 1.11 (s) | 1.11 (s) | 1.22 (s) | 1.18 (s) |
| 1' | | | | | |
| 2' | 4.26 (d, 10.0) | 4.58 (d, 8.5) | 4.54 (d, 9.0) | 6.48 (d, 16.0) | 6.50 (d, 16.0) |
| 3' | 4.58 (d, 10.0) | 4.93 (d, 8.5) | 4.92 (d, 9.0) | 7.67 (d, 16.0) | 7.68 (d, 16.0) |
| 3'-OCH$_2$CH$_3$ | 3.35 (q, 7.0) | | | | |
| 3'-OCH$_2$CH$_3$ | 1.06 (t, 7.0) | | | | |
| 4' | | | | | |
| 5' | 7.39 (m) | 7.39 (dd, 8.0, 2.0) | 7.40 (dd, 8.0, 1.5) | 7.60 (m) | 7.61 (m) |
| 6' | 7.39 (m) | 7.36 (dd, 8.0, 7.0) | 7.35 (m) | 7.39 (brdd, 3.5, 3.0) | 7.40 (brdd, 3.5, 3.0) |
| 7' | 7.39 (m) | 7.31 (d, 7.0) | 7.35 (m) | 7.39 (brdd, 3.5, 3.0) | 7.40 (brdd, 3.5, 3.0) |
| 8' | 7.39 (m) | 7.36 (dd, 8.0, 7.0) | 7.35 (m) | 7.39 (brdd, 3.5, 3.0) | 7.40 (brdd, 3.5, 3.0) |
| 9' | 7.39 (m) | 7.39 (dd, 8.0, 2.0) | 7.40 (dd, 8.0, 1.5) | 7.60 (m) | 7.61 (m) |
| 1" | | | | | |
| 2" | 4.13 (s) | 4.12 (s) | 4.11 (s) | | 4.14 (brs) |

Compd 1. 2'-Chloroenglerin A
Compd 2. 2'-Chloro,3'-hydroxydihydroenglerin A (epimer 1)
Compd 3. 2'-Chloro,3'-hydroxydihydroenglerin A (epimer 2)
Compd 4. 2',3'-Dichlorodihydroenglerin A (epimer 1)
Compd 5. 2',3'-Dichlorodihydroenglerin A (epimer 2)
Compd 6. 2'-Chloro,3'-ethoxydihydroenglerin A
Compd 7. 2'-Chloro,3'-hydroxydihydroenglerin A (epimer 3)
Compd 8. 2'-Chloro,3'-hydroxydihydroenglerin A (epimer 4).

Example 5

This Example demonstrates that compounds or epimers in accordance with embodiments of the invention inhibit cell growth of human tumor cell lines.

Biological activity of the compound fractions is assessed by 2-day cell growth assays using the sensitive human renal line UO-31 and the insensitive human CNS tumor cell line SF-295. Thus, fractions which lack the differential sensitivity can be readily distinguished from those which are more potent against the renal cell line. The primary endpoints of these assays are the formazan XTT, or alternatively, and in preference, the protein stain sulforhodamine B. All samples are tested in eight 10-fold dilutions with no drug and no-cell controls on each microtiter plate. IC$_{50}$ values are calculated using SOFTMAX™ software as supplied by the manufacturer of the microplate reader. The results are set forth in Table 3.

TABLE 3

Cell growth assay data on SF-295 and UO-31 cancer cell lines

| Compound | SF-295 IC$_{50}$ μM | UO-31 IC$_{50}$ μM | Selectivity SF-295/UO-31 |
|---|---|---|---|
| 2'-Chloroenglerin A | 72 | 0.92 | 78 |
| 2'-Chloro,3'-hydroxydihydroenglerin (epimer 1) | >100 | 0.96 | >104 |
| 2'-Chloro,3'-hydroxydihydroenglerin (epimer 2) | 92 | 8.7 | 11 |
| 2',3'-Dichlorodihydroenglerin A (epimer 1) | 90 | 1.2 | 75 |
| 2',3'-Dichlorodihydroenglerin A (epimer 2) | 60 | 0.75 | 80 |
| 2'-Chloro,3'-ethoxydihydroenglerin A | 35 | 18 | 1.94 |

TABLE 3-continued

Cell growth assay data on SF-295 and UO-31 cancer cell lines

| Compound | SF-295 IC$_{50}$ µM | UO-31 IC$_{50}$ µM | Selectivity SF-295/UO-31 |
|---|---|---|---|
| 2'-Chloro,3'-hydroxydihydroenglerin (epimer 3) | 42 | 0.41 | 102 |
| 2'-Chloro,3'-hydroxydihydroenglerin (epimer 4) | 20 | 16 | 1.25 |
| Englerin B | >100 | >100 | — |

Example 6

This Example illustrates that englerins and englerin derivatives of the invention inhibit human cancer cell growth. Samples are tested in the standard National Cancer Institute 60-cell line protocol. First, they are tested against all 60 cell lines in a single final concentration of 10 micromolar. Then, they are separately tested in five 10-fold dilutions. The drug exposure is two days, with an SRB endpoint. The results are set forth in Table 4.

TABLE 4

Potency of several englerins in renal cancer cell lines within the NCI 60 cell assay (GI$_{50}$ values µM).

| Renal Cell Line | 2'-Chloro-englerin A | 2'-Chloro,3'-hydroxy-dihydro-englerin (epimer 1) | 2'-Chloro,3'-hydroxy-dihydro-englerin (epimer 2) | 2',3'-Dichlorodihydroenglerin A (epimer 1) | 2',3'-Dichloro-dihydroenglerin A (epimer 2) |
|---|---|---|---|---|---|
| 786-0 | 10 | 1.7 | 11 | 12 | 12 |
| A498 | 0.028 | 0.18 | 0.66 | 0.14 | 0.049 |
| ACHN | 0.041 | 0.32 | 1.38 | 0.14 | 0.32 |
| CAKI-1 | 0.035 | 0.46 | 9.3 | 0.42 | 0.32 |
| RXF-393 | 0.019 | 0.51 | 0.39 | 0.93 | 0.32 |
| SN12C | 0.56 | 0.63 | 4.7 | 1.0 | 1.0 |
| TK-10 | 21 | 17 | 27 | 18 | 25 |
| UO-31 | 0.035 | 0.25 | 1.9 | 0.39 | — |
| Mean | 3.96 | 2.58 | 7.07 | 4.09 | 5.55 |
| Median | 0.04 | 0.49 | 3.32 | 0.68 | 0.32 |
| Geometric Mean | 0.21 | 0.70 | 3.13 | 0.94 | 0.72 |
| All 60 mean GI-50 | 5.6 | 6.9 | 12.0 | 8.3 | 11.7 |

Example 7

This example illustrates a method of preparing and characterizing englerin B monoacetate.

A sample (1.9 g) of englerin B was stirred in pyridine (0.25 mL) and acetic anhydride (0.25 mL) overnight at room temperature. The solvents were evaporated under vacuum and the product extracted in dichloromethane. The crude product was purified on pTLC (Si gel 60 F254; 2% MeOH/DCM) to give englerin B monoacetate (2.0 mg, 95%). The NMR data are set forth in Table 5. In a 2-cell assay englerin B monoacetate showed an approximate 400-fold selectivity against renal cancer cell line A498.

TABLE 5

NMR (DMSO-d$_6$, 500 MHz) Assignments For Englerin B Acetate

| # | δ$_H$ (m, J (Hz)) | δ$_C$ |
|---|---|---|
| 1 | 1.68 (m) | 47.1 |
| 2a | 1.64 (m) | 24.1 |
| 2b | 1.17 (m) | |
| 3a | 1.93 (m) | 30.5 |
| 3b | 1.15 (m) | |
| 4 | 2.03 (m) | 30.6 |
| 5 | 1.58 (m) | 45.9 |
| 6 | 4.97 (d, 10.0) | 70.6 |
| 7 | | 84.6 |
| 8a | 2.62 (dd, 14.0, 8.0) | 39.4 |
| 8b | 1.72 (dd, 14.0, 1.0) | |
| 9 | 5.09 (brd, 7.0) | 74.3 |
| 10 | | 84.1 |
| 11 | 0.85 (d, 7.0) | 16.6 |
| 12 | 1.80 (m) | 32.5 |
| 13 | 0.94 (d, 7.0) | 17.2 |
| 14 | 0.88 (d, 7.0) | 18.0 |
| 15 | 1.11 (s) | 18.7 |
| 1' | | 165.2 |
| 2' | 6.60 (d, 16.5) | 117.8 |
| 3' | 7.68 (d, 16.5) | 145.1 |
| 4' | | 133.9 |
| 5' | 7.72 (m) | 128.4 |
| 6" | 7.43 (m) | 128.9 |
| 7' | 7.43 (m) | 130.6 |
| 8' | 7.43 (m) | 128.9 |
| 9' | 7.72 (m) | 128.4 |
| 1" | | 170.0 |
| 2" | 2.05 (s) | 20.8 |

Example 8

This example illustrates renal cancer cell growth inhibition by englerin A, which showed excellent selectivity for the renal cancer cell line in the NCI-60 cell panel, with 5 of the 8 renal lines having $GI_{50}$ values under 20 nM.

TABLE 6

Cell growth inhibition data of englerin A

| Renal Cell Line | $GI_{50}$, µM |
|---|---|
| 786-0 | <0.01 |
| A498 | <0.01 |
| ACHN | <0.01 |
| CAKI-1 | 15.5 |
| RXF-393 | 0.011 |
| SN12C | 0.087 |
| TK-10 | 15.5 |
| UO-31 | <0.01 |
| Mean | 3.89 |
| Median | 0.01 |
| Geometric Mean | 0.08 |
| All 60 mean GI-50 | 2.82 |

Example 9

This example illustrates some of the properties of englerin A in accordance with an embodiment of the invention. FIG. 1A-1I depict the dose response curves for englerin A against various cancer cell lines in a 60-cell test, showing that the compound is active against a number of leukemia, non-small cell, colon cancer, melanoma, prostate, renal, breast, ovarian, and CNS cancer cell lines.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified compound of the formula:

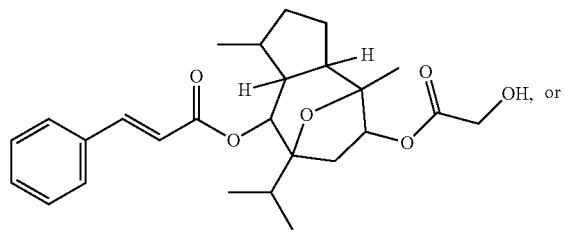

Englerin A

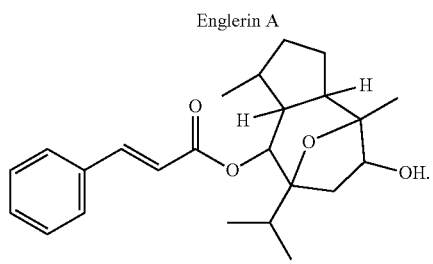

Englerin B

2. The isolated or purified compound of claim 1, which is Englerin A.

3. The isolated or purified compound of claim 1, which is Englerin B.

4. A compound of the formula (I):

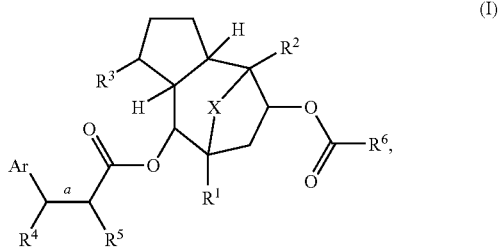

or an epimer thereof; wherein

Ar is an aryl group, optionally substituted with a $C_1$-$C_6$ alkyl, $C_1$-$C_6$ hydroxyalkyl, $C_1$-$C_6$ alkoxy, halo, or nitro;

X is O, NH, or S;

$R^2$ and $R^3$ are independently a $C_1$-$C_6$ alkyl;

$R^1$ is isopropyl or isopropylenyl;

"a" is a single bond or a double bond;

when "a" is a double bond, $R^4$ is hydrogen, and $R^5$ is halo or H;

when "a" is a single bond, $R^4$ is selected from the group consisting of halo, hydroxy, or $C_1$-$C_6$ alkoxy and $R^5$ is halo or H;

and $R^6$ is $C_1$-$C_6$ alkyl or hydroxy $C_1$-$C_6$ alkyl.

5. The compound or epimer of claim 4, wherein $R^6$ is hydroxy $C_1$-$C_6$ alkyl.

6. The compound of claim 4, which is

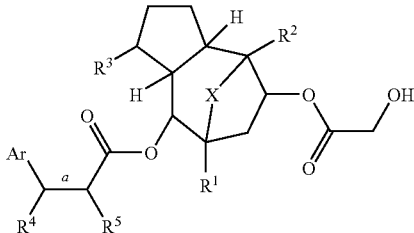

or an epimer thereof.

7. The compound or epimer of claim 4, wherein $R^5$ is halo.

8. The compound or epimer of claim 4, wherein $R^5$ is chloro.

9. The compound or epimer of claim 6, wherein Ar is phenyl, optionally substituted with a $C_1$-$C_6$ alkyl, $C_1$-$C_6$ hydroxyalkyl, $C_1$-$C_6$ alkoxy, halo, or nitro.

10. The compound or epimer of claim 4, wherein X is O.

11. The compound or epimer of claim 4, wherein $R^1$ is isopropyl.

12. The compound or epimer of claim 4, wherein "a" is a double bond and the double bond is E, Z, or a mixture of E and Z.

13. The compound or epimer of claim 4, wherein "a" is a single bond.

14. The compound or epimer of claim 13, wherein $R^4$ is hydroxy, chloro, or ethoxy.

15. The compound or epimer of claim 4, wherein $R^2$ and $R^3$ are methyl.

16. The compound or epimer of claim 4, which is:

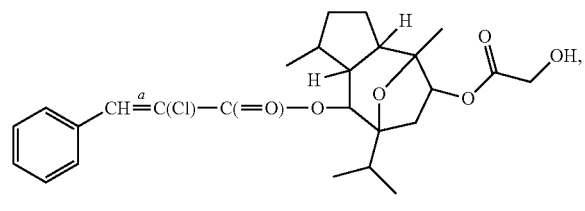

2'-Chloroenglerin A

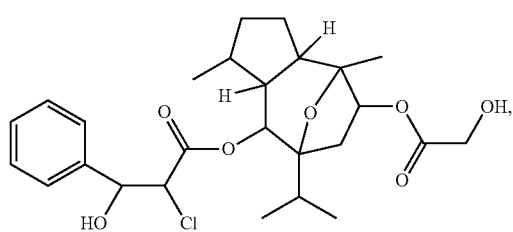

2'-Chloro,3'-hydroxydihydroenglerin A
(epimer 1, 2, 3, or 4)

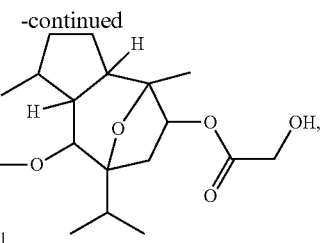

2',3'-Dichlorodihydroenglerin A
(epimer 1 or 2) or

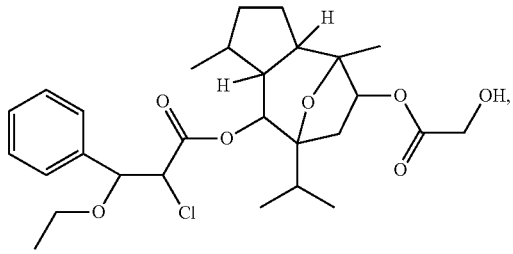

2'-Chloro,3'-ethoxydihydroenglerin A wherein the double bond "a" in 2'-Chloroenglerin A can be E, Z, or E/Z.

17. The compound or epimer of claim 4, wherein $R^6$ is $C_1$-$C_6$ alkyl.

18. A pharmaceutical composition comprising a pharmaceutically acceptable carrier and a compound of claim 1.

19. A method of treating cancer in an animal comprising administering to the animal an effective amount of a compound of claim 1.

20. The method of claim 19, wherein the animal is a human.

21. The method of claim 19, wherein the cancer is selected from the group consisting of leukemia, non-small cell lung cancer, colon cancer, melanoma, prostate cancer, renal cancer, breast cancer, CNS cancer, and ovarian cancer.

22. The method of claim 21, wherein the cancer is renal cancer.

23. The compound or epimer of claim 5, wherein Ar is phenyl, optionally substituted with a $C_1$-$C_6$ alkyl, $C_1$-$C_6$ hydroxyalkyl, $C_1$-$C_6$ alkoxy, halo, or nitro.

24. The compound or epimer of claim 6, wherein Ar is phenyl, optionally substituted with a $C_1$-$C_6$ alkyl, $C_1$-$C_6$ hydroxyalkyl, $C_1$-$C_6$ alkoxy, halo, or nitro.

25. The compound or epimer of claim 5, wherein X is O.

26. The compound or epimer of claim 6, wherein X is O.

27. The compound or epimer of claim 5, wherein $R^1$ is isopropyl.

28. The compound or epimer of claim 5, wherein "a" is a double bond and the double bond is E, Z, or a mixture of E and Z.

29. The compound or epimer of claim 5, wherein "a" is a single bond.

30. The compound or epimer of claim 29, wherein $R^4$ is hydroxy, chloro, or ethoxy.

31. The compound or epimer of claim 5, wherein $R^2$ and $R^3$ are methyl.

32. The compound or epimer of claim 5, wherein $R^6$ is $C_1$-$C_6$ alkyl.

33. A pharmaceutical composition comprising a pharmaceutically acceptable carrier and a compound or epimer of claim 4.

34. A pharmaceutical composition comprising a pharmaceutically acceptable carrier and a compound or epimer of claim 6.

35. A pharmaceutical composition comprising a pharmaceutically acceptable carrier and a compound or epimer of claim 16.

36. A method of treating cancer in an animal comprising administering to the animal an effective amount of a compound or epimer of claim 4.

37. A method of treating cancer in an animal comprising administering to the animal an effective amount of a compound or epimer of claim 6.

38. A method of treating cancer in an animal comprising administering to the animal an effective amount of a compound or epimer of claim 16.

39. The method of claim 36, wherein the animal is a human.

40. The method of claim 39, wherein the cancer is selected from the group consisting of leukemia, non-small cell lung cancer, colon cancer, melanoma, prostate cancer, renal cancer, breast cancer, CNS cancer, and ovarian cancer.

* * * * *